(12) United States Patent
Jablonski et al.

(10) Patent No.: US 8,486,134 B2
(45) Date of Patent: Jul. 16, 2013

(54) BIFURCATION TREATMENT SYSTEM AND METHODS

(75) Inventors: Brian Jablonski, White Bear Lake, MN (US); Jay Rassat, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 751 days.

(21) Appl. No.: 11/832,394

(22) Filed: Aug. 1, 2007

(65) Prior Publication Data
US 2009/0036830 A1 Feb. 5, 2009

(51) Int. Cl.
*A61F 2/06* (2006.01)

(52) U.S. Cl.
USPC ....... 623/1.35; 623/1.11; 623/1.23; 623/1.24; 623/1.27

(58) Field of Classification Search
USPC .................. 623/1.11, 1.23, 1.24, 1.27, 1.35
See application file for complete search history.

(56) References Cited

U.S. PATENT DOCUMENTS

| | | |
|---|---|---|
| 3,872,893 A | 3/1975 | Roberts et al. |
| 4,140,126 A | 2/1979 | Choudhury |
| 4,309,994 A | 1/1982 | Grunwald |
| 4,410,476 A | 10/1983 | Redding |
| 4,413,989 A | 11/1983 | Schjeldahl et al. |
| 4,421,810 A | 12/1983 | Rasmussen |
| 4,453,545 A | 6/1984 | Inoue |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,759,748 A | 7/1988 | Reed |
| 4,762,128 A | 8/1988 | Rosenbluth |
| 4,769,029 A | 9/1988 | Patel |
| 4,819,664 A | 4/1989 | Nazari |

(Continued)

FOREIGN PATENT DOCUMENTS

| | | |
|---|---|---|
| CA | 2318314 | 7/1999 |
| DE | 9014845 | 9/1991 |

(Continued)

OTHER PUBLICATIONS

Serruys et al., "A Comparison of Balloon Expandable-Stent Implantation with Balloon Angioplasty in Patients with Coronary Artery Disease," The New England Journal of Medicine, vol. 331, No. 8, pp. 489-495, Aug. 25, 1994.

(Continued)

*Primary Examiner* — Gary Jackson
*Assistant Examiner* — Kevin Everage
(74) *Attorney, Agent, or Firm* — Seager, Tufte & Wickhem LLC

(57) ABSTRACT

A catheter assembly configured for treatment of a vessel bifurcation. The catheter assembly includes a catheter shaft and first and second balloons. The second balloon extends radially outward relative to the first balloon when expanded. A valve arrangement controls expansion of the second balloon. Portions of the valve arrangement can be positioned at proximal and distal end portions of the catheter shaft. Typically, the first balloon is expanded followed by expansion of the second balloon. A stent having a lateral branch opening is operatively mounted to the first balloon. The second balloon is configured to extend through the lateral branch opening when the second balloon is expanded.

9 Claims, 5 Drawing Sheets

U.S. PATENT DOCUMENTS

| | | |
|---|---|---|
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz |
| 4,946,464 A | 8/1990 | Pevsner |
| 4,957,501 A | 9/1990 | Lahille |
| 4,957,508 A | 9/1990 | Kaneko et al. |
| 4,964,850 A | 10/1990 | Bouton |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,654 A | 2/1992 | Buell |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang et al. |
| 5,122,125 A | 6/1992 | Deuss |
| 5,135,536 A | 8/1992 | Hillstead |
| 5,147,317 A | 9/1992 | Shank |
| 5,159,920 A | 11/1992 | Condon et al. |
| 5,176,617 A | 1/1993 | Fischell |
| 5,192,297 A | 3/1993 | Hull |
| 5,195,984 A | 3/1993 | Schatz |
| 5,211,683 A | 5/1993 | Maginot |
| 5,217,440 A | 6/1993 | Frassica |
| 5,226,913 A | 7/1993 | Pinchuk |
| 5,234,457 A | 8/1993 | Andersen |
| 5,236,446 A | 8/1993 | Dumon |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,457 A | 6/1994 | Zhang |
| 5,337,733 A | 8/1994 | Bauerfeind |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,856 A | 1/1995 | Bersin |
| 5,383,892 A | 1/1995 | Cardon et al. |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,694 A | 10/1995 | Marin |
| 5,456,712 A | 10/1995 | Maginot |
| 5,456,714 A | 10/1995 | Owen |
| 5,458,608 A | 10/1995 | Wortrich |
| 5,462,530 A | 10/1995 | Jang |
| 5,476,471 A | 12/1995 | Shifrin et al. |
| 5,489,271 A | 2/1996 | Andersen |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau et al. |
| 5,507,769 A | 4/1996 | Marin |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie |
| 5,545,132 A | 8/1996 | Fagan |
| 5,549,553 A | 8/1996 | Ressemann et al. |
| 5,549,554 A | 8/1996 | Miraki |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,625 A | 3/1997 | Piplani et al. |
| 5,609,627 A | 3/1997 | Goicoechea et al. |
| 5,609,629 A | 3/1997 | Fearnot et al. |
| 5,613,891 A | 3/1997 | Lamo |
| 5,613,949 A | 3/1997 | Miraki |
| 5,613,980 A | 3/1997 | Chauhan |
| 5,617,878 A | 4/1997 | Taheri |
| 5,626,600 A | 5/1997 | Horzewski |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Marcade |
| 5,676,697 A | 10/1997 | McDonald |
| 5,679,400 A | 10/1997 | Tuch |
| 5,683,451 A | 11/1997 | Lenker et al. |
| 5,690,642 A | 11/1997 | Osborne |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon |
| 5,709,713 A | 1/1998 | Richoux |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,749,825 A | 5/1998 | Fischell et al. |
| 5,749,848 A | 5/1998 | Jang et al. |
| 5,755,734 A | 5/1998 | Richter |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall |
| 5,800,450 A | 9/1998 | Lary |
| 5,800,508 A | 9/1998 | Goicoechea et al. |
| 5,814,061 A | 9/1998 | Osborne |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,041 A | 10/1998 | Lenker et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |

| | | | | | | |
|---|---|---|---|---|---|---|
| 5,843,160 | A | 12/1998 | Rhodes | 6,258,121 B1 | 7/2001 | Yang et al. |
| 5,843,164 | A | 12/1998 | Frantzen et al. | 6,261,273 B1 | 7/2001 | Ruiz |
| 5,846,204 | A | 12/1998 | Solomon | 6,261,305 B1 | 7/2001 | Marotta et al. |
| 5,851,210 | A | 12/1998 | Torossian | 6,261,319 B1 | 7/2001 | Kveen et al. |
| 5,851,464 | A | 12/1998 | Davila et al. | 6,264,682 B1 | 7/2001 | Wilson et al. |
| 5,855,600 | A | 1/1999 | Alt | 6,273,911 B1 | 8/2001 | Cox et al. |
| 5,855,601 | A | 1/1999 | Bessler et al. | 6,273,913 B1 | 8/2001 | Wright et al. |
| 5,865,178 | A | 2/1999 | Yock | 6,287,314 B1 | 9/2001 | Lee |
| 5,868,777 | A | 2/1999 | Lam | 6,290,673 B1 | 9/2001 | Shanley |
| 5,871,537 | A | 2/1999 | Holman et al. | 6,293,967 B1 | 9/2001 | Shanley |
| 5,871,936 | A | 2/1999 | Chu | 6,299,634 B1 | 10/2001 | Bergeron |
| 5,891,133 | A | 4/1999 | Murphy-Chutorian | 6,302,906 B1 | 10/2001 | Goicoechea et al. |
| 5,897,588 | A | 4/1999 | Hull et al. | 6,309,412 B1 | 10/2001 | Lau et al. |
| 5,906,640 | A | 5/1999 | Penn et al. | 6,309,414 B1 | 10/2001 | Rolando et al. |
| 5,907,893 | A | 6/1999 | Zadno-Azizi et al. | 6,312,459 B1 | 11/2001 | Huang et al. |
| 5,913,895 | A | 6/1999 | Burpee et al. | 6,325,821 B1 | 12/2001 | Gaschino et al. |
| 5,913,897 | A | 6/1999 | Corso et al. | 6,325,826 B1 | 12/2001 | Vardi et al. |
| 5,921,958 | A | 7/1999 | Ressemann et al. | 6,334,870 B1 | 1/2002 | Ehr et al. |
| 5,922,020 | A | 7/1999 | Klein et al. | 6,346,089 B1 | 2/2002 | Dibie |
| 5,928,248 | A | 7/1999 | Acker | 6,350,279 B1 | 2/2002 | McGuinness |
| 5,938,682 | A | 8/1999 | Hojeibane et al. | 6,355,060 B1 | 3/2002 | Lenker et al. |
| 5,938,696 | A | 8/1999 | Goicoechea et al. | 6,361,544 B1 | 3/2002 | Wilson et al. |
| 5,948,016 | A | 9/1999 | Jang | 6,361,555 B1 | 3/2002 | Wilson |
| 5,951,599 | A | 9/1999 | McCrory | 6,371,978 B1 | 4/2002 | Wilson |
| 5,967,986 | A | 10/1999 | Cimochowski | 6,383,213 B2 | 5/2002 | Wilson et al. |
| 5,972,018 | A | 10/1999 | Israel et al. | 6,383,215 B1 | 5/2002 | Sass |
| 6,007,517 | A | 12/1999 | Anderson | 6,387,120 B2 | 5/2002 | Wilson et al. |
| 6,013,054 | A | 1/2000 | Jiun Yan | 6,395,018 B1 | 5/2002 | Castaneda |
| 6,013,091 | A | 1/2000 | Ley et al. | 6,398,792 B1 | 6/2002 | O'Connor |
| 6,017,324 | A | 1/2000 | Tu | 6,398,804 B1 | 6/2002 | Spielberg |
| 6,017,363 | A | 1/2000 | Hojeibane | 6,428,567 B2 | 8/2002 | Wilson et al. |
| 6,024,763 | A | 2/2000 | Lenker et al. | 6,428,570 B1 | 8/2002 | Globerman |
| 6,030,414 | A | 2/2000 | Taheri | 6,432,133 B1 | 8/2002 | Lau et al. |
| 6,033,434 | A | 3/2000 | Borghi | 6,436,104 B2 | 8/2002 | Hojeibane |
| 6,033,435 | A | 3/2000 | Penn et al. | 6,436,134 B2 | 8/2002 | Richter |
| 6,036,682 | A | 3/2000 | Lange | 6,468,302 B2 | 10/2002 | Cox et al. |
| 6,039,749 | A | 3/2000 | Marin | 6,475,208 B2 | 11/2002 | Mauch |
| 6,042,597 | A | 3/2000 | Kveen et al. | 6,478,816 B1 | 11/2002 | Kveen et al. |
| 6,045,557 | A | 4/2000 | White | 6,482,211 B1 | 11/2002 | Choi |
| 6,048,361 | A | 4/2000 | Von Oepen | 6,485,511 B2 | 11/2002 | Lau et al. |
| 6,056,775 | A | 5/2000 | Borghi | 6,494,905 B1 | 12/2002 | Zedler et al. |
| 6,059,823 | A | 5/2000 | Holman et al. | 6,508,836 B2 | 1/2003 | Wilson et al. |
| 6,059,824 | A | 5/2000 | Taheri | 6,511,504 B1 | 1/2003 | Lau et al. |
| 6,066,168 | A | 5/2000 | Lau et al. | 6,511,505 B2 | 1/2003 | Cox et al. |
| 6,068,655 | A | 5/2000 | Seguin et al. | 6,520,988 B1 | 2/2003 | Colombo et al. |
| 6,071,285 | A | 6/2000 | Lashinski et al. | 6,527,799 B2 | 3/2003 | Shanley |
| 6,086,611 | A | 7/2000 | Duffy et al. | 6,540,719 B2 | 4/2003 | Bigus et al. |
| 6,090,127 | A | 7/2000 | Globerman | 6,540,779 B2 | 4/2003 | Richter et al. |
| 6,090,128 | A | 7/2000 | Douglas | 6,572,647 B1 | 6/2003 | Supper et al. |
| 6,096,073 | A | 8/2000 | Webster et al. | 6,579,309 B1 | 6/2003 | Loos et al. |
| 6,099,497 | A | 8/2000 | Adams et al. | 6,579,312 B2 | 6/2003 | Wilson et al. |
| 6,102,929 | A | 8/2000 | Conway et al. | 6,582,394 B1 | 6/2003 | Reiss et al. |
| 6,117,117 | A | 9/2000 | Mauch | 6,582,459 B1 | 6/2003 | Lau et al. |
| 6,117,156 | A | 9/2000 | Richter et al. | 6,596,022 B2 | 7/2003 | Lau et al. |
| 6,126,685 | A | 10/2000 | Lenker et al. | 6,599,315 B2 | 7/2003 | Wilson |
| 6,129,738 | A | 10/2000 | Lashinski et al. | 6,599,316 B2 | 7/2003 | Vardi et al. |
| 6,129,754 | A | 10/2000 | Kanesaka et al. | 6,602,254 B2 | 8/2003 | Gertzbein |
| 6,142,973 | A | 11/2000 | Carleton et al. | 6,641,609 B2 | 11/2003 | Globerman |
| 6,152,945 | A | 11/2000 | Bachinski et al. | 6,645,241 B1 | 11/2003 | Strecker |
| 6,165,195 | A | 12/2000 | Wilson et al. | 6,652,973 B2 | 11/2003 | Ota et al. |
| 6,165,197 | A | 12/2000 | Yock | 6,669,717 B2 | 12/2003 | Marotta et al. |
| 6,165,214 | A | 12/2000 | Lazarus | 6,676,667 B2 | 1/2004 | Mareiro et al. |
| 6,179,867 B1 | | 1/2001 | Cox | 6,679,911 B2 | 1/2004 | Burgermeister |
| 6,183,506 B1 | | 2/2001 | Penn et al. | 6,689,156 B1 | 2/2004 | Davidson et al. |
| 6,190,403 B1 | | 2/2001 | Fischell et al. | 6,692,483 B2 | 2/2004 | Vardi et al. |
| 6,193,746 B1 | | 2/2001 | Strecker | 6,695,877 B2 | 2/2004 | Brucker et al. |
| 6,203,569 B1 | | 3/2001 | Wijay | 6,706,062 B2 | 3/2004 | Vardi et al. |
| 6,210,380 B1 | | 4/2001 | Mauch | 6,709,440 B2 | 3/2004 | Callol et al. |
| 6,210,429 B1 | | 4/2001 | Vardi | 6,719,720 B1 * | 4/2004 | Voelker et al. ............. 604/99.02 |
| 6,217,527 B1 | | 4/2001 | Selmon et al. | 6,736,841 B2 | 5/2004 | Musbach et al. |
| 6,217,608 B1 | | 4/2001 | Penn et al. | 6,770,092 B2 | 8/2004 | Richter |
| 6,221,080 B1 | | 4/2001 | Power | 6,780,174 B2 | 8/2004 | Mauch |
| 6,221,090 B1 | | 4/2001 | Wilson | 6,802,856 B2 | 10/2004 | Wilson |
| 6,221,098 B1 | | 4/2001 | Wilson et al. | 6,827,735 B2 | 12/2004 | Greenberg |
| 6,231,563 B1 | | 5/2001 | White et al. | 6,827,736 B2 | 12/2004 | Perouse |
| 6,241,762 B1 | | 6/2001 | Shanley | 6,852,124 B2 | 2/2005 | Cox |
| 6,258,073 B1 | | 7/2001 | Mauch | 6,855,125 B2 | 2/2005 | Shanley |
| 6,258,099 B1 | | 7/2001 | Mareiro et al. | 6,872,215 B2 | 3/2005 | Crocker |
| 6,258,116 B1 | | 7/2001 | Hojeibane | 6,908,477 B2 | 6/2005 | McGuckin, Jr. |

| | | |
|---|---|---|
| 6,942,689 B2 | 9/2005 | Majercak |
| 6,958,051 B2 * | 10/2005 | Hart et al. ............... 604/100.01 |
| 7,056,323 B2 | 6/2006 | Mareiro et al. |
| 7,105,019 B2 | 9/2006 | Hojeibane |
| 7,118,593 B2 | 10/2006 | Davidson et al. |
| 7,125,419 B2 | 10/2006 | Sequin et al. |
| 7,163,553 B2 | 1/2007 | Limon |
| 7,220,275 B2 | 5/2007 | Davidson et al. |
| 7,238,917 B2 | 7/2007 | Stava |
| 7,244,853 B2 | 7/2007 | Schreiber et al. |
| 7,252,679 B2 | 8/2007 | Fischell et al. |
| 7,387,639 B2 | 6/2008 | Bourang et al. |
| 7,585,317 B2 | 9/2009 | Davidson et al. |
| 2001/0012927 A1 | 8/2001 | Mauch |
| 2001/0016767 A1 | 8/2001 | Wilson et al. |
| 2001/0016768 A1 | 8/2001 | Wilson et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0037146 A1 | 11/2001 | Lau et al. |
| 2001/0037147 A1 | 11/2001 | Lau et al. |
| 2001/0039395 A1 | 11/2001 | Mareiro et al. |
| 2001/0039448 A1 | 11/2001 | Dibie |
| 2001/0047201 A1 | 11/2001 | Cox et al. |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0032478 A1 | 3/2002 | Boekstegers et al. |
| 2002/0035392 A1 | 3/2002 | Wilson |
| 2002/0042650 A1 | 4/2002 | Vardi et al. |
| 2002/0052648 A1 | 5/2002 | McGuckin, Jr. et al. |
| 2002/0058990 A1 | 5/2002 | Jang |
| 2002/0072790 A1 | 6/2002 | McGuckin, Jr. et al. |
| 2002/0107564 A1 | 8/2002 | Cox et al. |
| 2002/0111675 A1 | 8/2002 | Wilson |
| 2002/0123790 A1 | 9/2002 | White et al. |
| 2002/0123797 A1 | 9/2002 | Majercak |
| 2002/0123798 A1 | 9/2002 | Burgermeister |
| 2002/0151959 A1 | 10/2002 | Von Oepen |
| 2002/0156516 A1 | 10/2002 | Vardi et al. |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0177892 A1 | 11/2002 | Globerman |
| 2002/0183763 A1 | 12/2002 | Callol et al. |
| 2002/0193872 A1 | 12/2002 | Trout, III et al. |
| 2002/0193873 A1 | 12/2002 | Brucker et al. |
| 2003/0004535 A1 | 1/2003 | Musbach et al. |
| 2003/0009209 A1 | 1/2003 | Hojeibane |
| 2003/0009214 A1 | 1/2003 | Shanley |
| 2003/0014102 A1 | 1/2003 | Hong et al. |
| 2003/0023301 A1 | 1/2003 | Cox et al. |
| 2003/0028211 A1 | 2/2003 | Crocker et al. |
| 2003/0050688 A1 | 3/2003 | Fischell et al. |
| 2003/0074047 A1 | 4/2003 | Richter |
| 2003/0093109 A1 | 5/2003 | Mauch |
| 2003/0114912 A1 | 6/2003 | Sequin et al. |
| 2003/0114915 A1 | 6/2003 | Mareiro et al. |
| 2003/0125791 A1 | 7/2003 | Sequin et al. |
| 2003/0125799 A1 | 7/2003 | Limon |
| 2003/0125802 A1 | 7/2003 | Callol et al. |
| 2004/0015227 A1 | 1/2004 | Vardi et al. |
| 2004/0049259 A1 | 3/2004 | Strecker |
| 2004/0072849 A1 | 4/2004 | Schreiber et al. |
| 2004/0133268 A1 | 7/2004 | Davidson et al. |
| 2004/0138737 A1 | 7/2004 | Davidson et al. |
| 2004/0148006 A1 | 7/2004 | Davidson et al. |
| 2005/0015108 A1 | 1/2005 | Williams et al. |
| 2005/0060027 A1 | 3/2005 | Khenansho et al. |
| 2005/0102019 A1 * | 5/2005 | Yadin ............................. 623/1.11 |
| 2007/0100301 A1 | 5/2007 | Gumm |

FOREIGN PATENT DOCUMENTS

| | | |
|---|---|---|
| DE | 29701758 | 5/1997 |
| EP | 0884028 | 12/1998 |
| EP | 0891751 | 1/1999 |
| EP | 0897700 | 2/1999 |
| EP | 0904745 | 3/1999 |
| EP | 1031328 | 8/2000 |
| EP | 1254644 | 11/2002 |
| EP | 0646365 | 1/2004 |
| EP | 0684022 | 2/2004 |
| EP | 0897698 | 6/2004 |
| EP | 0551179 | 4/2005 |
| EP | 1157674 | 7/2005 |
| EP | 0804907 | 11/2005 |
| EP | 1031330 | 11/2005 |
| EP | 0876805 | 8/2006 |
| FR | 2678508 | 1/1993 |
| WO | 9013332 | 11/1990 |
| WO | 9112779 | 9/1991 |
| WO | 9219308 | 11/1992 |
| WO | 9508965 | 4/1995 |
| WO | 9521592 | 8/1995 |
| WO | 9629955 | 10/1996 |
| WO | 9641592 | 12/1996 |
| WO | 9709946 | 3/1997 |
| WO | 9716217 | 5/1997 |
| WO | 9726936 | 7/1997 |
| WO | 9732544 | 9/1997 |
| WO | 9733532 | 9/1997 |
| WO | 9741803 | 11/1997 |
| WO | 9745073 | 12/1997 |
| WO | 9817204 | 4/1998 |
| WO | 9819628 | 5/1998 |
| WO | 9835634 | 8/1998 |
| WO | 9836709 | 8/1998 |
| WO | 9837833 | 9/1998 |
| WO | 9844871 | 10/1998 |
| WO | 9848733 | 11/1998 |
| WO | 9852497 | 11/1998 |
| WO | 9915103 | 4/1999 |
| WO | 9917680 | 4/1999 |
| WO | 9924104 | 5/1999 |
| WO | 9934749 | 7/1999 |
| WO | 9936002 | 7/1999 |
| WO | 9939661 | 8/1999 |
| WO | 9958059 | 11/1999 |
| WO | 9965419 | 12/1999 |
| WO | 0000104 | 1/2000 |
| WO | 0012166 | 3/2000 |
| WO | 0013613 | 3/2000 |
| WO | 0053122 | 9/2000 |
| WO | 0074595 | 9/2000 |
| WO | 0121095 | 3/2001 |
| WO | 0121109 | 3/2001 |
| WO | 0121244 | 3/2001 |
| WO | 0170299 | 9/2001 |
| WO | 02068012 | 9/2002 |
| WO | 02076333 | 10/2002 |
| WO | 02094336 | 11/2002 |
| WO | 03037417 | 5/2003 |
| WO | 03055414 | 7/2003 |
| WO | 2004026180 | 4/2004 |
| WO | 2005041810 | 5/2005 |
| WO | 2005/082440 | 9/2005 |
| WO | 2006033126 | 3/2006 |

OTHER PUBLICATIONS

Fischman et al., "A Randomized Comparison of Coronary-Stent Placement and Balloon Angioplasty in the Treatment of Coronary Artery Disease," New England Journal of Medicine, vol. 331, No. 8, pp. 496-501, Aug. 25, 1994.

Nakamura et al., "Techniques for Palmaz-Schatz Stent Deployment in Lesions with a Large Side Branch," Catheterization and Cardiovascular Diagnosis, vol. 34, pp. 353-361, 1995.

Caputo et al., "Stent Jail: A Minimum-Security Prison," The American Journal of Cardiology, vol. 77, pp. 1226-1230, Jun. 1, 1996.

Carrie et al., ""T"-Shaped Stent Placement: A Technique for the Treatment of Dissected Bifurcation Lesions," Catheterization and Cardiovascular Diagnosis, vol. 37, pp. 311-313, 1996.

Colombo et al., ""Kissing" Stents for Bifurcational Coronary Lesion," Catheterization and Cardiovascular Diagnosis, vol. 30, pp. 327-330, 1993.

Katoh et al., "New Double Wire Technique to Stent Ostial Lesions," Catheterization and Cardiovascular Diagnosis, vol. 40, pp. 400-402, 1997.

Lewis et al., "Acute Procedural Results in the Treatment of 30 Coronary Artery Bifurcation Lesions with a Double-Wire Atherectomy Technique for Side-Branch Protection," American Heart Journal, vol. 127, No. 6, pp. 1600-1607, 1994.

Dichek et al., "Seeding of Intravascular Stents with Genetically Engineered Endothelial Cells," Circulation, vol. 80, No. 5, pp. 1347-1353, Nov. 1989.

Chevalier et al., "Placement of Coronary Stents in Bifurcation Lesions by the "Culotte" Technique," The American Journal of Cardiology, vol. 82, pp. 943-949, Oct. 15, 1998.

Satler et al. "Bifurcation Disease: To Treat or Not to Treat," Catheterization and Cardiovascular Interventions, vol. 50, pp. 411-412, 2000.

Yamashita et al., "Bifurcation Lesions: Two Stents Versus One Stent—Immediate and Follow-up Results," Journal of the American College of Cardiology, vol. 35, No. 5, pp. 1145-1151, Apr. 2000.

* cited by examiner

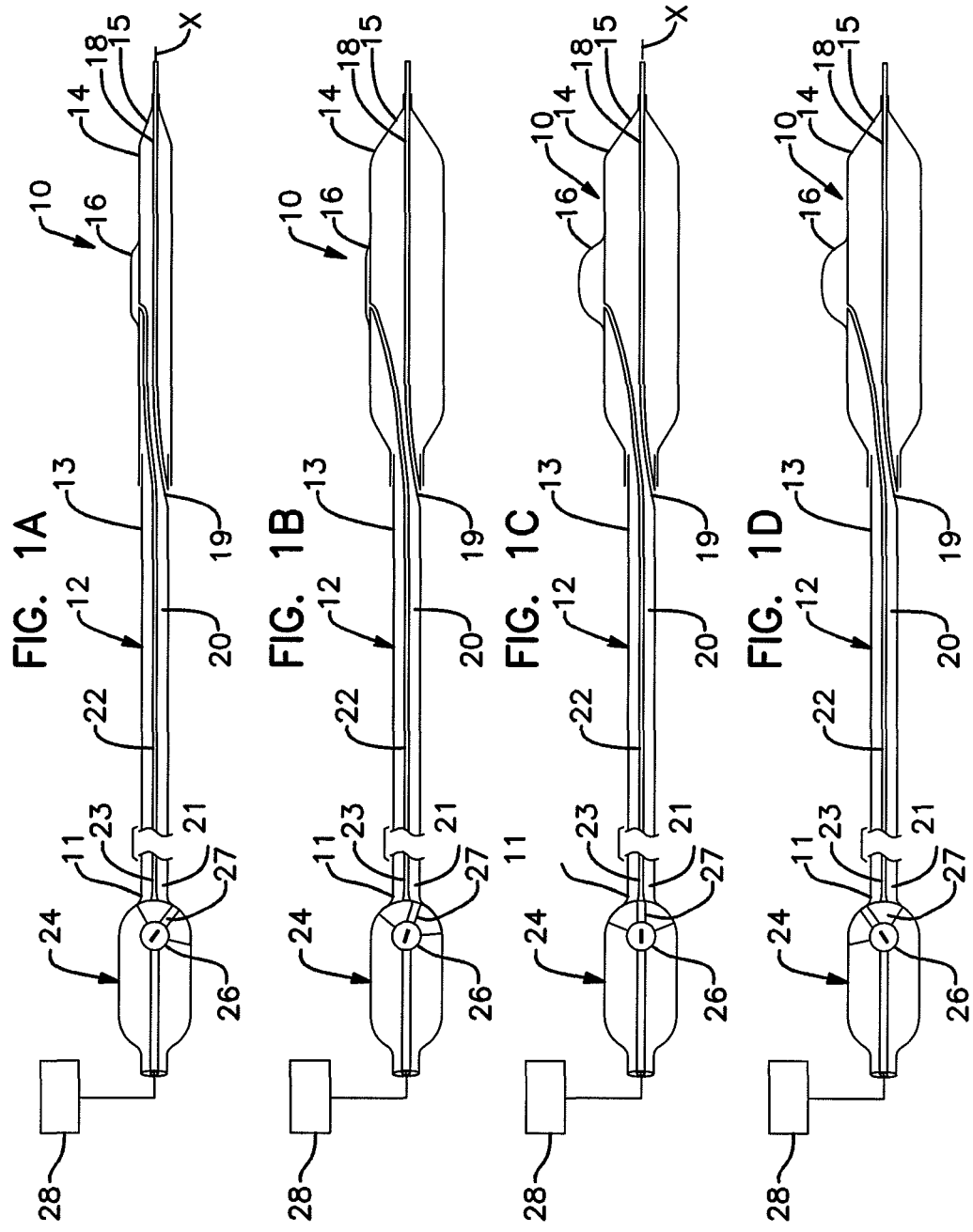

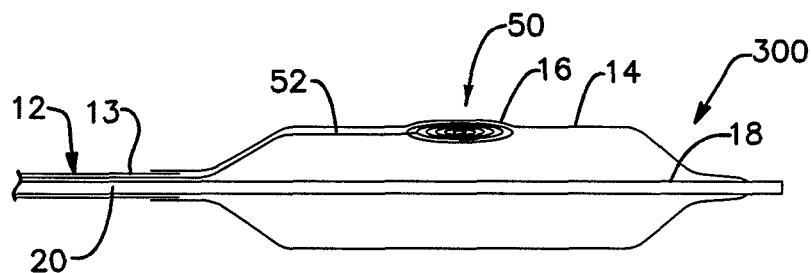
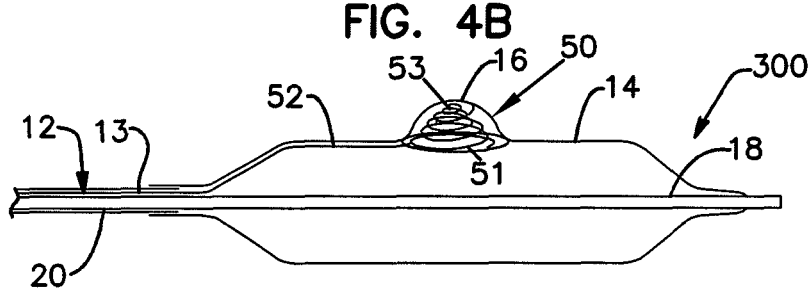
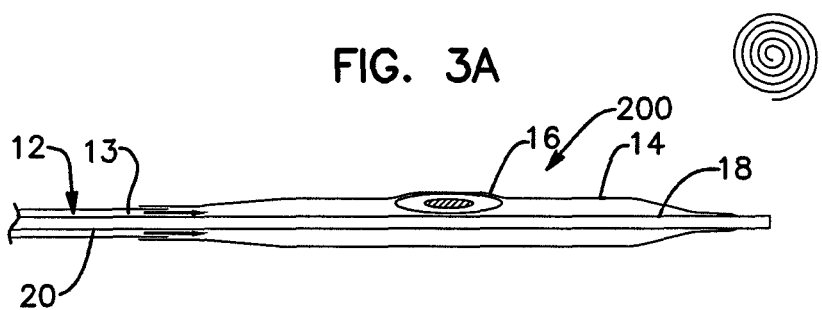
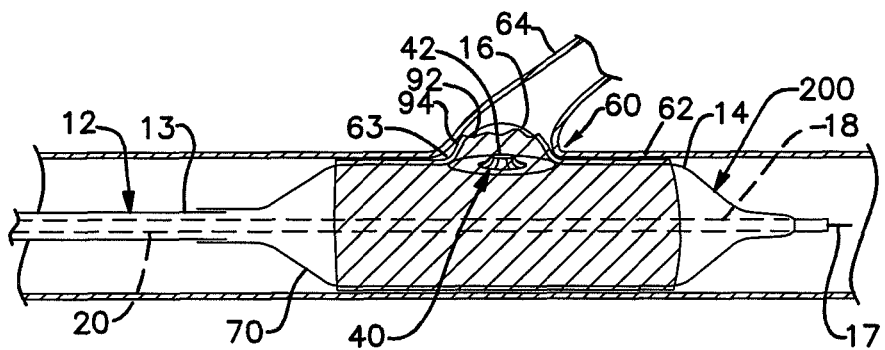

BIFURCATION TREATMENT SYSTEM AND METHODS

TECHNICAL FIELD

This disclosure relates to bifurcation treatment systems and related methods of treating a bifurcation. Preferred arrangements also relate to methods and configurations for activating balloon portions of catheter assemblies used to treat vessel bifurcations.

BACKGROUND

Catheters are used with stents and balloon structures to treat strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular body organ for treating conditions such as, for example, occlusions, stenoses, aneurysms, dissection, or weakened, diseased, or abnormally dilated vessel or vessel wall, by expanding the vessel or by reinforcing the vessel wall. Stents can improve angioplasty results by preventing elastic recoil and remodeling of the vessel wall and treating dissections in blood vessel walls caused by balloon angioplasty of coronary arteries.

While conventional stent technology is relatively well developed, stent technologies related to treatment of the region of a vessel bifurcation are still being developed.

SUMMARY OF THE DISCLOSURE

The present disclosure relates generally to catheter assemblies for treatment of bifurcated lumens in a patient, such as a vessel bifurcation. One aspect of the present disclosure relates to a catheter assembly having first and second balloons. The first balloon is an elongate tubular structure coupled to a distal end of a catheter shaft and the second balloon is positioned on the first balloon. The second balloon can extend radially outward relative to the first balloon. In one arrangement, a layer or membrane is provided between the first and second balloons to control relative timing of inflation of the first and second balloons. Typically, the first balloon is inflated followed by the creation of an opening in the membrane that provides fluid flow between the first and second balloons to radially extend the second balloon.

A further aspect of the present disclosure relates to a valve mechanism in a manifold that is in fluid communication with proximal ends of at least two inflation lumens of the catheter assembly. The inflation lumens are in fluid communication with first and second balloon portions of the catheter assembly. The valve mechanism controls the flow of inflation fluid from a fluid source to one of the inflation lumens at a time. The valve can also be actuated into an OFF position in which fluid flow from the fluid source to all inflation lumens is terminated. The valve can also be used to deflate or re-inflate the first and second balloon portions.

BRIEF DESCRIPTION OF THE DRAWINGS

FIG. 1A is a schematic side view of an example catheter assembly constructed according to principles of this disclosure and having a valve member in a first closed position;

FIG. 1B is a schematic side view of the catheter assembly shown in FIG. 1, wherein the valve member is in a first open position in fluid communication with a primary inflation lumen;

FIG. 1C is a schematic side view of the catheter assembly shown in FIG. 1, wherein the valve member is in a second open position in fluid communication with a secondary inflation lumen;

FIG. 1D is a schematic side view of the catheter assembly shown in FIG. 1, wherein the valve member is in a second closed position;

FIG. 3A is a schematic side view of distal end features of another example catheter assembly according to principles of this disclosure, the catheter assembly including a valve structure in a closed configuration at a location between deflated first and second balloon members;

FIG. 4A is a schematic side view of distal end features of another example catheter assembly according to principles of this disclosure, wherein a mechanical expansion member is positioned within a deflated second balloon member and the first balloon member is inflated;

FIG. 4B is a schematic side view of the catheter assembly shown in FIG. 4A, wherein the mechanical expansion member is activated to expand the second balloon;

FIG. 4C is a top view of the mechanical expansion member of FIG. 4B.

FIG. 7 is a schematic side view of the catheter assembly shown in FIG. 3C and having a stent positioned thereon, the catheter assembly being positioned within a vessel bifurcation.

DETAILED DESCRIPTION

I. General Background

Figure 2A:
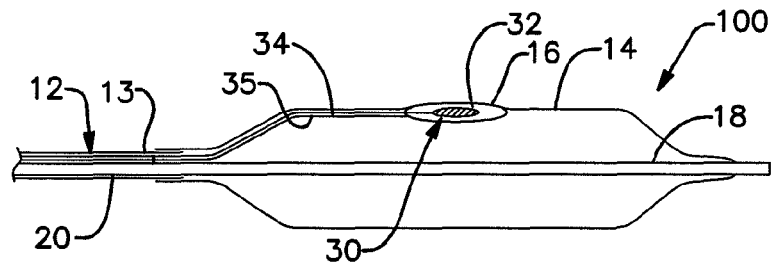
FIG. 2A is a schematic side view of distal end features of a catheter assembly according to principles of this disclosure, the catheter assembly including a valve structure in a closed configuration at a location between an inflated first balloon member and a deflated second balloon member.

This disclosure relates to catheter assemblies for treatment of bifurcations and related methods of treating bifurcations in a patient's body. The term bifurcation means a division point from one unit into two or more units. Generally, bifurcations of a body lumen are defined as 1) a continuous main lumen having at least one branch lumen that extends or branches off from the main lumen, or 2) a first lumen (also referred to as a parent lumen) that splits into at least first and second branch lumens. The term lumen means the cavity of a tubular structure. An example bifurcation is a vessel bifurcation that includes a continuous main vessel and a branch vessel that branches off from the main vessel. A vessel bifurcation can alternatively include a parent vessel that divides into first and second branch vessels.

Some of the example catheter assemblies disclosed herein include a main catheter shaft or other structure that defines an inflation lumen, a guidewire housing that defines a guidewire lumen, and an elongate main balloon positioned at a distal end portion of the catheter shaft. A secondary balloon is also positioned at the distal end portion of the catheter shaft. In some arrangements, the secondary balloon is positioned on the main balloon. The secondary balloon, when inflated, protrudes in a generally radial direction relative to a longitudinal axis of the main balloon. A secondary balloon that is "positioned on" the main balloon is mounted to the main balloon or integral with the main balloon. FIGS. 1A-4B illustrate some example secondary balloons that are positioned on a main balloon.

Other example catheter assemblies disclosed herein include a secondary or side balloon that is positioned on a separate side inflation member that extends in parallel with and adjacent to the main balloon. The secondary balloon, when inflated, protrudes in a generally radial direction relative to a longitudinal axis of the main balloon. A proximal end portion of the side inflation member can intersect the catheter shaft proximal of the main balloon. The side inflation member can also be in fluid communication with an inflation lumen that provides inflation fluid to the main balloon. In some arrangements, the side inflation lumen remains exterior of the catheter shaft proximal of the main balloon. The side inflation member can also remain fluidly separated from the inflation lumen that provides inflation fluid to the main balloon. FIGS. 5A-6C illustrate some example secondary balloons that are positioned along a separate side inflation member.

The side inflation member and the inflation lumen that provides inflation fluid to the main balloon can be coupled at a proximal end portion of the catheter shaft to a manifold having a valve mechanism. An example manifold is described below with reference to FIGS. 1A-D.

The example catheter assemblies disclosed herein can further include a stent. The catheter assemblies can be adapted to position the stent at a bifurcation treatment site in the area of, for example, a vessel bifurcation. The stent can include proximal and distal open ends, and a lateral branch opening. The lateral branch opening is positioned at a location between the proximal and distal open ends of the stent. At least a portion of the secondary balloon extends through the lateral branch opening when the secondary balloon is expanded radially outward from the main balloon.

The term "balloon" as used herein is not limited to an inflatable member that expands when filed with an inflation fluid (e.g., liquid or gaseous substance). A balloon as used herein is an expandable member that is expanded from an unexpanded state to an expanded state using any one of a variety of mediums, structures, and methods. Typically, the balloons described herein are configured for use in a body lumen such as a blood vessel. Further, the balloons described herein can be used to expand portions of an expandable stent that is operably mounted to or in engagement with at least a portion of the balloon when the balloon is expanded.

II. The Example Illustrated in FIGS. 1A-D

An example catheter assembly 10 is now described with reference to FIGS. 1A-D. The catheter assembly 10 includes a catheter shaft 12, first and second balloons 14, 16, a guidewire housing that defines a guidewire lumen 18, and primary and secondary inflation members 20, 22 that define primary and second inflation lumens, respectively. The term "inflation lumen" is used herein interchangeably with the term "inflation member". A manifold 24 is coupled to a proximal end portion 11 of the catheter shaft 12. The manifold 24 includes a valve 26 that is adjustable between first, second, third and fourth positions illustrated in FIGS. 1A-D, respectively, to control the flow of inflation fluid to the balloons 14, 16.

The first and second balloons 14, 16 are positioned at a distal end portion 13 of the catheter shaft 12. The first balloon 14 typically has an elongate tubular shape with a generally circular cross-section. The second balloon 16 is positioned on an exterior of the first balloon 14 and is inflatable to expand in a generally radial direction relative to a longitudinal axis X of the first balloon 14 (see FIG. 1C.

The primary inflation lumen 20 is defined within an interior cavity of the catheter shaft 12. The primary inflation lumen 20 is in fluid communication with an interior of the first balloon 14. The secondary inflation lumen 22 is also shown defined within the catheter shaft 12 between proximal and distal end portions 11, 13 of the catheter shaft 12. Secondary inflation lumen 22 is coupled in fluid communication with the second balloon 16. The inflation lumens 20, 22 can be separate tubes positioned in parallel with each other and arranged within the catheter shaft 12. Alternatively, the inflation lumens 20, 22 can be defined within the catheter shaft by a longitudinally arranged dividing wall within the catheter shaft 12. In other arrangements, one of the inflation lumens 20, 22 can be positioned outside of the catheter shaft 12. The primary and secondary inflation lumens 20, 22 are coupled in fluid communication at the proximal end portion of the catheter shaft 12 to a source of inflation fluid 28 via the valve 26 of manifold 24. Typically, the inflation lumens 20, 22 are fluidly separated from each other.

The guidewire lumen 18 extends through the first balloon 14 and distally beyond a distal end 15 of the first balloon 14. The guidewire lumen 18 is shown exiting the first balloon 14 and catheter shaft 12 at the distal end portion of the catheter shaft 12. This type of construction for the guidewire lumen 18 is sometimes referred to as a single operator exchange (SOE) guidewire system such as a rapid exchange (Rx) guidewire system. In other arrangements, the guidewire lumen 18 extends within the catheter shaft 12 from the distal end portion to the proximal end portion of the catheter shaft 12 and through the first balloon 14.

The valve 26 of manifold 24 is configured for adjustment in several different positions to control fluid flow from the fluid source 28 to the balloons 14, 16. FIG. 1A illustrates the valve 26 in a first closed position in which a fluid path 27 through the valve 26 is not in fluid communication with open proximal end portions 21, 23 of the primary and secondary inflation lumens 20, 22. FIG. 1B illustrates the valve 26 in a second position in which the fluid path 27 is aligned with open end 21 into the primary inflation lumen 20. FIG. 1C illustrates the valve 26 in a third position in which a fluid path 27 is aligned with the open end 23 into the secondary inflation lumen 22 to provide fluid communication between the fluid source 28 and the second balloon 16. FIG. 1D illustrates the valve 26 in a fourth position in which the fluid path 27 is again no longer in fluid communication with either the primary or secondary inflation lumens 20, 22. While not illustrated in the attached Figures, it is possible in alternative arrangements to simultaneously provide fluid communication between the fluid source 28 and each of the balloons 14, 16 via one or more of the inflation lumens 20, 22.

The valve 26 is configured as a rotatable structure having a fluid path that is in fluid communication with only one of the primary or secondary inflation lumens 20, 22 at any given time. The structure of the valve 26 shown in FIGS. 1A-D is schematic and provided for illustrative purposes only. Other example valve structures may be used to provide a similar valving function. Further aspects of the valve 26 will be described now with reference to a method of using the catheter assembly 10.

When the catheter assembly 10 is used for treatment within a patient, the first and second balloons 14, 16 are typically initially maintained in a deflated state as shown in FIG. 1A to have a minimum outer profile or circumference. Providing a minimum outer profile improves the ability of the catheter assembly 10 to travel through various body lumens such as a coronary vessel. When the distal end portion of the catheter shaft 12 has been located at a treatment site within a patient, the first and second balloons are inflated for purposes of treating the bifurcation.

Referring now to FIG. 1B, the first balloon 14 is inflated first by adjusting the valve 26 from the first (closed) position in which the fluid source 28 is disconnected from fluid communication with either of the primary and secondary inflation lumens 20, 22 (see FIG. 1A), to a second position in which the fluid source 28 is coupled in fluid communication with the primary inflation lumen 20. After the first balloon 14 has been inflated, the valve 26 is adjusted to the third position as shown in FIG. 1C to provide fluid communication between the fluid source 28 and the secondary inflation lumen 22.

After the second balloon 16 has been inflated, the valve 26 can be adjusted into various positions as desired. For example, the valve 26 can be adjusted into the fourth position shown in FIG. 1D in which the fluid source 28 is again disconnected from fluid communication with the primary and secondary inflation lumens 20, 22. The valve 26 can also be adjusted from the third position shown in FIG. 1C to the second position shown in FIG. 1B to provide additional inflation of the first balloon 14. The valve 26 can also be adjusted from the third position to the first position shown in FIG. 1A.

The valve 26 can also be adjusted into any of the positions shown in FIGS. 1A-D when deflating the first and second balloons 14, 16. When deflating the first and second balloons 14, 16, the valve 26 can be coupled to a depository for inflation fluid. In some cases, the fluid source 28 can act as the fluid depository, while in other arrangements a separate fluid depository can be provided. When deflating the first and second balloons 14, 16, the valve 26 can be adjusted between the position shown in FIGS. 1A-D as desired to sequentially deflate first and second balloons 14, 16. The first and second balloons 14, 16 can be deflated completely in one step or can be deflated in multiple steps by switching between the positions shown in FIGS. 1A-D.

In the catheter assemblies disclosed herein, the balloons, when inflated within a vessel, can be used to treat conditions such as stenosis and plaque buildup within the vessel. The balloons can be constructed of any suitable material. Some example materials for the balloons and catheters disclosed herein include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, polyethylene terephthalate (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

A wide variety of stents, catheters, and guidewire configurations can be used with the bifurcation delivery system embodiments of the present disclosure. The inventive principles disclosed herein should not be limited to any particular design or configuration.

The catheter assembly 10 can be used in conjunction with an expandable stent (e.g., see stent 70 in FIG. 7 described below). Some example stents that can be used with the bifurcation delivery systems disclosed herein can be found in, for example, U.S. Pat. Nos. 6,210,429, 6,325,826 and 6,706,062 to Vardi et al., co-pending U.S. patent application Ser. No. 10/644,550, filed on Aug. 21, 2003, and titled STENT WITH A PROTRUDING BRANCH PORTION FOR BIFURCATED VESSELS, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

Typically, a stent is arranged on the first balloon 14 with the lateral branch opening of the stent aligned axially and radially with the second balloon 16. The second balloon 16, when inflated, extends through the lateral branch opening. Further discussion of stents with lateral branch openings and treatment of vessel bifurcations is described below with reference to FIG. 7.

III. The Example Illustrated in FIGS. 2A-B

Another example catheter assembly 100 is described with reference to FIGS. 2A-B. Catheter assembly 100 includes a catheter shaft 12, first and second balloons 14, 16, a guidewire lumen 18, an inflation lumen 20, and an electroactive polymer (EAP) valve 30. The catheter shaft 12 may have at its proximal end (not shown) a manifold or other instruments for manipulation of the catheter shaft 12. The first balloon 14 is coupled at its proximal end to a distal end portion of the catheter shaft 12. A distal end of the first balloon 14 is coupled to a distal end of the guidewire lumen 18. The inflation lumen 20 is in fluid communication with an interior of the first balloon 14.

The second balloon 16 is positioned on the first balloon 14 between proximal and distal ends of the first balloon 14. The second balloon 16 is configured to expand in a direction radially outward from the first balloon 14 upon inflation. In one example, the second balloon 16 can be formed integral with the first balloon 14 using, for example, a molding process. Alternatively, the second balloon 16 can be manufactured as a separate piece and secured or otherwise mounted to the first balloon 14 in a separate step using, for example, heat bonding or welding (e.g., laser bonding), adhesive bonding, or mechanical bonding (e.g., ultrasonic, radio frequency, lapping, or swaging). In a further alternative, the first and second balloons 14, 16 are formed as a two-piece balloon having an inner balloon and an outer balloon.

The valve 30 (or other valve structures disclosed herein) can be positioned between the first and second balloons 14, 16 concurrently with the molding process for a single piece or two piece balloon construction. Alternatively, the valve can be positioned during a secondary treatment of an inner layer of one of the balloons prior to joining with or within a second layer, for example, by cutting away a portion and replacing the cut away portion with a second piece that provides the valving function.

The EAP valve 30 includes an EAP material 32. A plurality of actuation wires 34, 35 can be electrically connected to the EAP material 32. Upon activation via one or both of the activation wires 34, 35, the EAP material 32 changes shape to define an opening 36 (see FIG. 2B).

Depending on the placement of the EAP material in the catheter assembly, a variety of characteristics can be manipulated and/or improved. EAP is characterized by its ability to change shape in response to electrical stimulations. When used as an actuator, an EAP material typically undergoes a large amount of deformation while sustaining large forces. EAP material can be classified as dielectric EAPs and ionic EAPs. Piezoelectric materials can also be employed, but tend to undergo deformation when voltage is applied. Electric EAPs include ferroelectric polymers, dielectric EAPs, electrorestrictive polymers such as the electrorestrictive graft elastomers and electroviscoelastic elastomers, and liquid crystal elastomer materials. Ionic EAPs include ionic polymer gels, ionomeric polymer-metal composites, conductive polymers and carbon nanotubes. Upon application of a small voltage, ionic EAPs can bend and change shape significantly.

Ionic EAPs also have a number of additional properties that make them attractive for use in the catheter assembly configurations disclosed herein, including the following: 1) they are relatively lightweight, flexible, small and easily manufactured; 2) energy sources are available that are easy to control, and energy can be easily delivered to the EAPs; 3) small changes in potential (e.g., potential changes on the order of 1V) can be used to effect volume change in the EAPs; 4) they are relatively fast in actuation (e.g., full expansion/contraction in a few seconds); 5) EAP regions can be created using a variety of techniques, for example, electrodeposition; and 6) EAP regions can be patterned, for example, using photolithography, if desired.

The following elements are commonly utilized to bring about EAP actuation: 1) a source of electrical potential, 2) an active region that comprises the EAP, 3) a counter electrode, and 4) an electrolyte in contact with both the active region and the counter electrode. The source of electrical potential for use in connection with the present invention can be quite simple, consisting, for example of a DC battery and an ON/OFF switch. Alternatively, more complex systems can be utilized. For example, an electrical link can be established with a microprocessor, allowing a complex set of control signals to be sent to the EAP active regions. The electrolyte, which is in contact with at least a portion of the surface of the active region, allows for the flow of ions and thus acts as a source/sink for the ions. Any suitable electrolyte can be employed herein. The electrolyte can be, for example, a liquid, a gel, or a solid, so long as ion movement is permitted. The counter electrode can be formed from any suitable electrical conductor, for example, a conducting polymer, a conducting gel, or a metal, such as stainless steel, gold, or platinum. At least a portion of the surface of the counter electrode is generally in contact with the electrolyte in order to provide a return path for charge.

In one arrangement, the EAP employed is polypyrrole. Polypyrrole-containing active regions can be fabricated using a number of known techniques, such as extrusion, casting, dip coating, spin coating, or electro-polymerization/deposition techniques. Such active regions can also be patterned, for example, using lithographic techniques, if desired. Other example EAP materials include polyaniline, polysulfone, and polyacetylene. Additional details and description related to EAP materials and their uses are described in commonly assigned copending U.S. patent application Ser. Nos. 11/411, 690 and 10/763,825, and U.S. Pat. No. 6,514,237, which are incorporated herein by reference in their entirety.

Figure 2B:
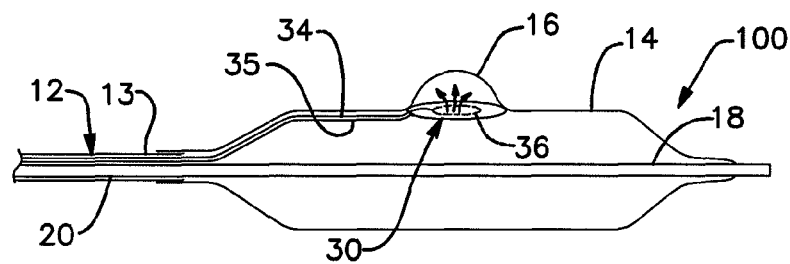
FIG. 2B is a schematic side view of the catheter assembly shown in FIG. 2A wherein the valve structure is in an open configuration to provide inflation of the second balloon member.

The actuation wires 34, 35 provide electronic actuation of the EAP material to change the EAP valve between the closed position shown in FIG. 2A in which there is no fluid flow between the first and second balloons 14, 16, and the open position shown in FIG. 2B in which the opening 36 provides fluid communication between the first and second balloons 14, 16. When the EAP valve 30 is in the open position shown in FIG. 2B, inflation fluid from within the first balloon 14 travels into the interior of the second balloon 16 to inflate the second balloon 16 into the radially extended position shown in FIG. 2B. In some arrangements, the EAP valve 30 can be closed to further control fluid flow between the first and second balloon 14, 16.

The actuation wires 34, 35 are shown extending from the EAP material 32, through the interior of the first balloon 14, and through the interior of the catheter shaft 12 towards a proximal location for actuation by an operator. In other arrangements, the actuation wire 34 can be positioned along a different path such as, for example, along an exterior of a portion of the first balloon 14 and the catheter shaft 12. In another example, the actuation wire 34 can extend through a portion of the second balloon 16 into engagement with the EAP material 32. The actuation wires can also be, for example, part of a braid of wire, a helical coil between inner and outer layers of the catheter shaft or other structures of the catheter assembly, or a pad printable conductive ink (or similar conductive material) that is transferred to the surface of the inner up to the location of the second balloon 16.

IV. The Example Illustrated in FIGS. 3A-C

Another example catheter assembly 200 is now described with reference to FIGS. 3A-C. Catheter assembly 200 includes many of the same or similar features as described above with reference to catheter assembly 100 except that the EAP valve 30 is replaced with a membrane 40 without EAP properties. The membrane 40 is positioned between the first and second balloons 14, 16. In one example, the membrane 40 is integrated into a side wall of the first balloon 14 that is at least partially enclosed by the balloon 16. The membrane 40 is configured to be modified or otherwise operated at some point during inflation of first balloon 14 to provide a fluid flow path between the interior of the first balloon 14 and an interior of the second balloon 16.

Figure 3B:
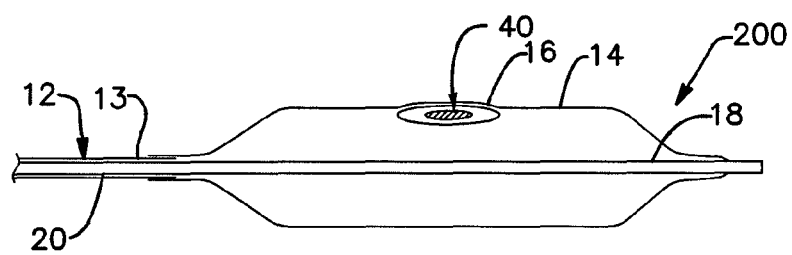
FIG. 3B is a schematic side view of the catheter assembly shown in FIG. 3A wherein the valve member is closed and the first balloon member is inflated.

FIG. 3A illustrates that catheter assembly 200 with the first and second balloons 14, 16 in a deflated state. FIG. 3B illustrates the first balloon 14 inflated via the inflation lumen 20. FIG. 3C illustrates the membrane 40 in a modified state in which an opening 42 is defined. Fluid flows from the first balloon 14 through the opening 42 into the second balloon 16 to inflate the second balloon 16 into the radially extended position.

The membrane 40 can be configured to generate the opening 42 in any of a plurality of different ways. For example, the membrane 40 can be configured to rupture automatically when a certain pressure threshold is reached within the first balloon 14. In another example, the membrane 40 can include stress lines that tear to provide at least one slit opening upon reaching a threshold pressure condition in the first balloon 14. In yet further examples, a mechanical structure can be coupled to the membrane 40 to puncture or otherwise initiate generation of the opening 42 at a desired point in time. In one arrangement, a pull member is connected to the membrane 40 at a distal end of the pull member, and a proximal end of the pull member is accessible by an operator of the catheter assembly 200. Pulling of the proximal end of the pull member creates the opening 42. An example pull member includes a cable or wire structure.

V. The Example Illustrated in FIGS. 4A-B

Another example catheter assembly 300 is described with reference to FIGS. 4A-B. The catheter assembly 300 has many of the same features as described above with reference to catheter assembly 100 except that the EAP valve 30 is replaced with a mechanical expansion member 50. The mechanical expansion member 50, upon activation, is configured to extend the second balloon 16 from a first non-deployed position shown in FIG. 4A to a deployed, radially extended position shown in FIG. 4B. Mechanical expansion member 50 is capable of moving the second balloon 16 into the radially extended position without the use of an inflation fluid. The mechanical expansion member 52 is positioned between the first and second balloons 14, 16. A first side 51 of the expansion member 50 engages an outer sidewall of the first balloon 14. A second side 53 of the expansion member 50 engages the second balloon 16. The expansion member 50 may be more effective at moving the second balloon 16 into the radially extended position shown in FIG. 4B when the first balloon 14 has already been at least inflated.

An activator 52 can be coupled to the mechanical expansion member 50 to initiate activation of the expansion member 50 from the non-deployed state shown in FIG. 4A to the deployed state shown in FIG. 4B. The activator 50, similar to the activation wire 34 shown in FIGS. 2A-B, extends within the first balloon 14 and catheter shaft 12 to a proximal location accessible by an operator of the catheter assembly 300. The activator 52 can have different functions depending on the type of mechanical expansion member 50 being used. For example, the activator 52 can be a pull wire that mechanically releases the mechanical expansion member 50 so that it can move from the non-deployed to deployed state. Alternatively, the activator 52 can be an electrical coupling that provides an electrical stimulus to the mechanical expansion member 50 that initiates the deployed state. The mechanical expansion member 50 can comprise a thermal shaped memory material such as Nitinol (Nickel Titanium Naval Ordnance Laboratory) that provides bimodal actuation initiated by an applied voltage or current. Thermal shape memory material provides for a change in shape of the mechanical expansion member 50 by heating the material above a transition temperature. The transition temperature for thermal shaped memory material Flexinol® made by Dynalloy of Costa Mesa, Calif. is about 70° C. The transition temperature of other thermal shaped memory materials can be higher or lower depending on the specific material composition.

When a thermal shaped memory material is cooled, it can be stretched or otherwise formed into a new shape different from the original shape. By including thermal shaped memory material in the construction of the mechanical expansion member 50, the original shape can be the extended, deployed configuration shown in FIG. 4B, and the shape maintained when below the transition temperature is the non-deployed state shown in FIG. 4A. Some types of thermal shaped memory material can be heated to its transition temperature using the body heat of the patient into which the catheter assembly 300 is introduced. Using the patient's body as the heat source, it is possible to estimate a range of time required to reach the transition temperature beginning with introduction of the catheter assembly 300 into the patient. Reducing the initial temperature of the mechanical expansion member 50 before introducing the catheter assembly 300 into the patient (e.g., by refrigeration) can help extend the time period required for reaching the transition temperature after the catheter assembly 300 has been introduced into the patient. As mentioned above, the thermal shaped memory material can also be heated using an electric current or other heat source besides the patient's body such as, for example, heat from the inflation fluid used to inflate the first balloon 14.

FIG. 4C illustrates a top view of the mechanical expansion member 50 in a coiled configuration. Other shapes and structures for mechanical expansion member 50 can be used such as, for example, a crown-type structure. The mechanical expansion member 50 can be bounded or otherwise secured to either or both of the first and second balloons 14, 16. Alternatively, the mechanical expansion member 50 can be loosely held in the space defined between the first and second balloons 14, 16.

VI. The Examples Illustrated in FIGS. 5A-6C

Figure 5A:
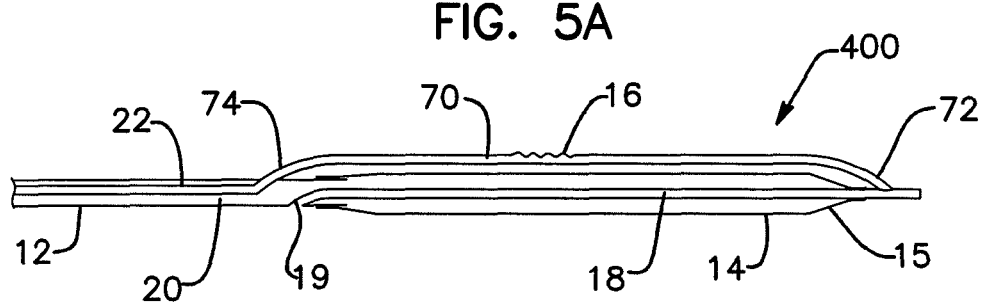
FIGS. 5A-C are schematic side views of distal end features of another example catheter assembly according to principles of this disclosure, wherein a side balloon is coupled to a separate side inflation member and fluidly separated from the main balloon.
Figure 5B:
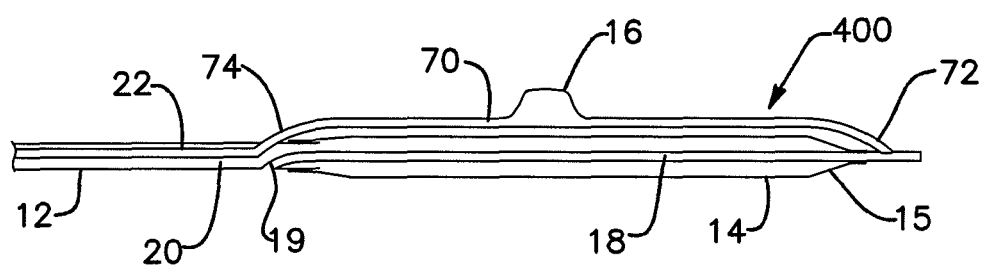
Figure 5C:
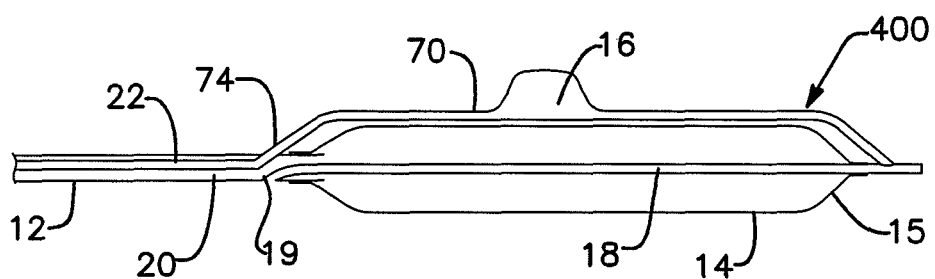

Another example catheter assembly 400 is described with reference to FIGS. 5A-C. The catheter assembly 400 has many of the same features as described above with reference to catheter assemblies 100, 200, 300 except that the second balloon 16 is positioned on a distal end portion 70 of the secondary inflation lumen 22. The distal end portion 70 of the secondary inflation lumen 22 has a distal end 72 that is secured to the guidewire housing that defines guidewire lumen 18 at a location distal of the main balloon distal end 15. The secondary inflation lumen 22 exits the catheter shaft 12 at a point 74 along the distal end portion 70. A proximal end portion of the secondary inflation lumen is in fluid communication with a manifold, such as manifold 24 shown in FIGS. 1A-D.

In other arrangements, the secondary inflation lumen 22 extends along an exterior of the catheter shaft 12 from the proximal end portion of the shaft 12 to the first balloon 14. The secondary inflation lumen 22 can be secured to the outer surface of the catheter shaft 12 or the first balloon 14 using, for example, heat bonding or adhesives. Further, the distal end 72 of the distal end portion 70 of the secondary inflation lumen 22 can be truncated and the distal end portion 70 secured to an exterior of the first balloon 14 at a location proximal or distal of the second balloon 16.

Inflation of the second balloon 16 can be controlled using any of the structures and configuration described above with reference to FIGS. 1-4C. For example, a valve structure such as an EAP valve can be positioned within the secondary inflation lumen, or a mechanical expansion member 50 can be positioned within the second balloon 16.

Other balloon structures and configurations can be used for the first and second balloons shown in FIGS. 1-5C using the principles disclosed herein. For example, the second balloon can be positioned on a separate catheter branch that is positioned within a branch vessel of a vessel bifurcation and inflated using the valving and inflation techniques discussed herein.

Figure 6A:
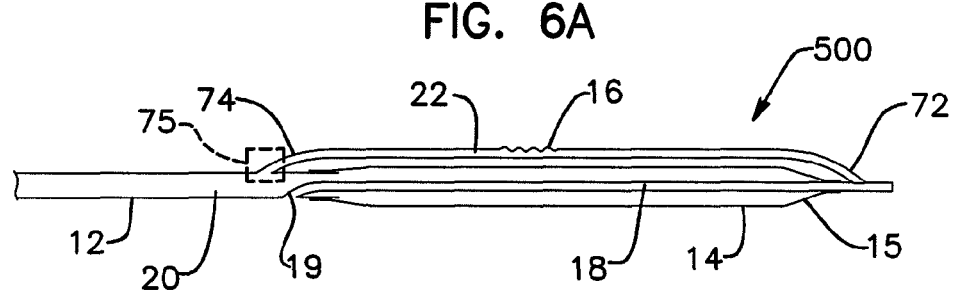
FIGS. 6A-C are schematic side views of distal end features of another example catheter assembly according to principles of this disclosure, wherein a side balloon is coupled to a separate side inflation member that is operable to be in fluid communication with the main balloon.
Figure 6B:
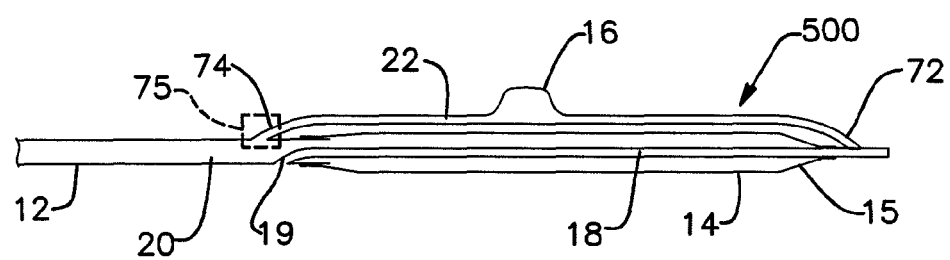
Figure 6C:
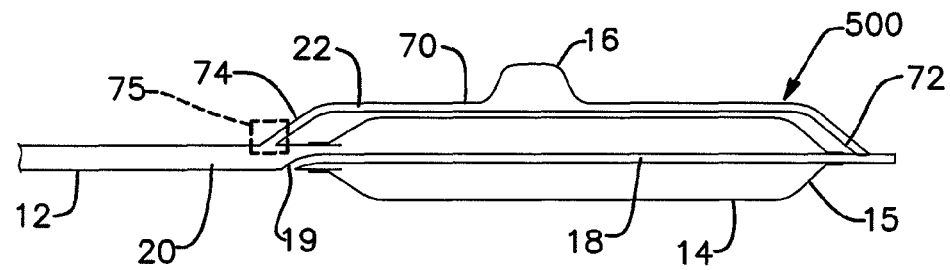

Referring now to FIGS. 6A-C, another example catheter assembly 500 is shown and described. Catheter assembly 500 includes many of the same or similar features as described above related to FIGS. 5A-C. The catheter assembly 500 includes a secondary inflation lumen 22 that provides inflation fluid to the secondary balloon 16. The secondary inflation lumen 22 intersects the inflation lumen 20 proximal of the main balloon 14 at a proximal end portion 74 of the secondary inflation lumen 22. A valve arrangement 75 is positioned along the secondary inflation lumen at a location between the inflation lumen 20 and the secondary balloon 16. The valve arrangement 75 is shown schematically in FIGS. 6A-C at a location where the secondary inflation lumen 22 intersects the distal end portion of the catheter shaft 12. Alternatively, the valve arrangement 75 can be positioned at other locations such as, for example, at or near a distal end portion 72 of the secondary inflation lumen 22.

The valve arrangement 75 can include any of the valve member configurations described above, for example, those configurations described with reference to FIGS. 1A-4C. For example, the valve arrangement 75 can include an EAP material, a pull member, or a pressure sensitive membrane.

VII. Example Vessel Bifurcation Treatment

Figure 3C:
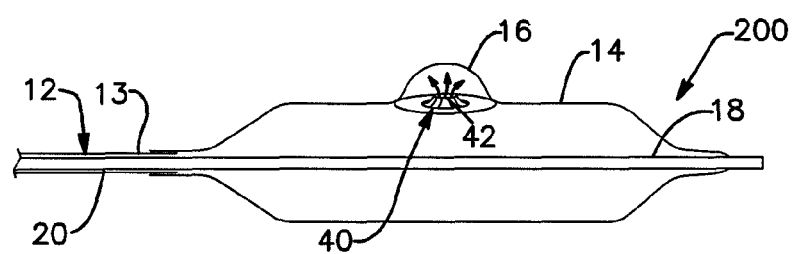
FIG. 3C is a schematic side view of the catheter assembly shown in FIG. 3A wherein the valve member is open and the first and second balloons members are inflated.

Referring now to FIG. 7, the catheter assembly 200 shown with reference to FIGS. 3A-C is shown in FIG. 7 in use with a stent 70 to treat a vessel bifurcation 60. The vessel bifurcation includes a main vessel 62 and a branch vessel 64 branching off of the main vessel 62. An ostium 63 of the branch vessel 64 is defined as the opening into the branch vessel 64 along a sidewall of the main vessel 62.

The stent 70 is an elongate tubular structure having opposing open ends. The stent 70 includes a plurality of structures along its length that permit expansion of the stent from an unexpanded state (not shown) to the expanded state shown in FIG. 7. Typically, the plurality of structures of the stent define a series of cell openings. In addition to the cell openings, the stent 90 includes a separate lateral branch opening 92 defined in a sidewall of the stent between the opposing open ends of the stent. The lateral branch opening 92 is usually larger than the cell opening, but can be the same or a smaller size than the cell openings. In one example, the lateral branch opening 92 is defined by a band of continuous material that defines a perimeter of the lateral branch opening 92. This continuous band of material preferably includes discontinuities over its length so that the area of the lateral branch opening 92 expands together with the expansion of the stent 90. In some configurations, the continuous band includes protrusions that project inwardly from a peripheral edge of the lateral branch opening 92. These protrusions (also referenced as expandable structure 94) are initially positioned within a cylindrical envelope of the tubular body of the stent 90. The expandable structure 94 can expand at least partially radially outward from a main body of the stent 90 outside of the cylindrical envelope of the main body of the stent 90 upon inflation of the second balloon 16.

The stent 90 is positioned on the first balloon 14 between proximal and distal ends of the balloon 14. The lateral branch opening 92 is aligned with the second balloon 16 such that moving the second balloon 16 into a radially extended position will cause the second balloon 16 to at least partially extend through the lateral branch opening 92 toward the ostium 63 of the branch vessel 64. Expanding the expandable structure 94 can extend that expandable structure 94 through the ostium of the branch vessel 64 to treat, for example, portions of the main and branch vessels 62, 64. Expanding the expandable structure 74 can provide a larger path through the lateral branch opening 92 of the stent 90 into the branch 64 for passage of additional treatment or alignment devices used after deflation of the first and second balloons 14, 16.

When treating the vessel 60, it is sometimes preferable to first fix the main body of the stent 90 within the main vessel 62 prior to expanding the expandable structures in the radially outward facing direction into the branch vessel 64. In order to ensure this sequence of expansion of features of the stent 90, a delay is provided for inflating or otherwise radial extending the balloon 16 until after the first balloon 14 has been fully inflated to expand the main body of the stent 90 into engagement with the main vessel 62. The use of, for example, the EAP valve 30 of FIGS. 2A-B, the openable membrane 40 shown in FIGS. 3A-C, or the mechanical expansion member 50 shown in FIGS. 4A-C described above can provide the desired sequence of first inflating the first balloon 14 followed by radially extending the second balloon 16. In the example shown in FIG. 7, the first balloon 14 is inflated to expand the main body of stent 90 followed by modification of the membrane 40 to create the opening 42 thereby inflating the second balloon 16 to radially extend the expandable structure 94.

The catheter assemblies 100, 200, 300, 400 described above can be used in conjunction with additional catheter components and features that help with aligning the stent lateral branch opening 92 with the ostium 63 of the branch vessel 64. For example, a side catheter branch that defines a branch guidewire lumen for receiving a branch guidewire can extend parallel with the catheter shaft 12 to the vessel bifurcation 60. The side catheter branch extends through the proximal open end of the stent 90, out of the lateral branch opening 92, and into the branch vessel 64. In an example method of treating vessel bifurcation 60, the guidewire 17 is located in the main vessel 62 distally of the ostium 63, and the branch guidewire is positioned within the branch vessel 64. The stent 90 is pre-positioned around the first and second balloons 14, 16 with the second balloon aligned with the lateral branch opening 92 of the stent 90. The side catheter branch is also pre-positioned extending through the lateral branch opening 92. The catheter assembly 10 with stent 90 and the side catheter branch are then advanced over the guidewire 17 and the branch guidewire to the vessel bifurcation 60. A distal end of the side catheter branch automatically advances into the branch vessel 64 over the branch guidewire as the catheter assembly 10 is positioned across the vessel bifurcation. The side catheter branch can help rotationally align the lateral branch opening 92 with the ostium 63 because it is extending through both the lateral branch opening 92 and the ostium 63.

Another catheter alignment feature that can be used with catheter assemblies 100, 200, 300 is a marker system. Positioning radiopaque markers along the side catheter branch (discussed above), the catheter shaft 12, and the balloon 14 can help the physician visualize under fluoroscopy when the side catheter branch has advanced into the branch vessel 64. Some example markers and marker materials are described in U.S. Pat. No. 6,692,483 to Vardi, et al., and co-pending U.S. Provisional Patent Application Ser. No. 60/776,149, filed on Feb. 22, 2006, and titled MARKER ARRANGEMENT FOR BIFURCATION CATHETER, which are incorporated herein by reference. For example, at least two axially spaced apart markers can be positioned on opposing ends of the balloon 14 and at least two markers positioned along the side catheter branch. Relative positioning of the four markers can provide information about relative radial position of the side catheter branch and catheter shaft 12, which can be used in axial and radial alignment of the balloon 16 and stent lateral branch opening 92 relative to the ostium 63 of branch vessel 64.

The stent 90 can be used in a similar way for treatment of a vessel bifurcation using the other catheter assemblies and principles disclosed herein.

V. Conclusion

On aspect of the present disclosure relates to catheter assembly having a catheter shaft, main and secondary balloons, and an actuator arrangement. The catheter shaft includes a distal end portion and a proximal end portion. The main balloon is positioned at the distal end portion of the catheter shaft. The main balloon is operable between an unexpanded configuration and an expanded configuration. The secondary balloon is also positioned at the distal end portion of the catheter shaft. The secondary balloon is operable between an unexpanded configuration in which the second balloon is positioned adjacent to the main balloon and an expanded configuration in which the second balloon extends radially outward relative to the main balloon. The actuator arrangement is configured to operate the secondary balloon between the unexpanded configuration to the expanded configuration independently of operation of the main balloon between the unexpanded and expanded configurations. The catheter assembly can further include a stent having a lateral branch opening. At least a portion of the secondary balloon extends through the lateral branch opening when the second balloon is in the expanded configuration. The actuator arrangement can have various configurations such as a membrane that ruptures when a threshold pressure condition is exceeded, a membrane that ruptures in response to an applied potential, a pull member configured to generate an opening in the membrane, or a mechanical actuator positioned within the secondary balloon that actuates the secondary balloon between the unexpanded and expanded configurations.

Another aspect of the present disclosure relates to a method of treating a vessel bifurcation with a catheter assembly. The vessel bifurcation includes a main vessel and a branch vessel extending from the main vessel. The catheter assembly includes a catheter shaft having proximal and distal end portions, a first balloon positioned at the distal end portion of the catheter shaft, a second balloon positioned at the distal end portion of the catheter shaft, and an actuator arrangement. The method steps include positioning the catheter assembly within the main vessel with the second balloon oriented facing an ostium of the branch vessel, inflating the first balloon, and after the step of inflating the first balloon, operating the actuator arrangement to expand the second balloon in a radially outward direction relative to the first balloon.

A further aspect of the present disclosure relates to another catheter assembly. The catheter assembly includes a catheter shaft having a proximal end portion and a distal end portion, a first balloon member positioned at the distal end portion of the catheter shaft, a second balloon member positioned at the distal end portion of the catheter shaft and configured to expand radially outward relative to the first balloon member, first and second inflation housings defining first and second inflation lumens, and a valve member. The first inflation lumen extends from the proximal end portion to the distal end portion of the catheter shaft. The first inflation lumen is coupled in fluid communication with the first balloon. The second inflation lumen extends from the proximal end portion to the distal end portion of the catheter shaft. The second inflation lumen is coupled in fluid communication with the second balloon. The valve member is adjustable between a first position connecting a fluid source in fluid communication with the first inflation lumen while preventing fluid communication between the fluid source and the second inflation lumen, a second position connecting the fluid source in fluid communication with the second inflation lumen while preventing fluid communication between the fluid source and the first inflation lumen, and a third position wherein the fluid source is not in fluid communication with the first and second inflation lumens.

A further aspect of the present disclosure relates to a method of operating a balloon catheter. The balloon catheter includes a catheter shaft having proximal and distal end portions, first and second balloons positioned at the distal end portion of the catheter shaft, and a manifold positioned at the proximal end portion of the catheter shaft. The second balloon is configured to extend radially outward relative to the first balloon. The method includes the step of operating the manifold to connect the first balloon in fluid communication with an inflation source while preventing fluid communication between the fluid source and the second balloon. The method further includes, after operating the manifold to connect the first balloon in fluid communication with the inflation source, operating the manifold to connect the second balloon in fluid communication with the inflation source while preventing fluid communication between the fluid source and the first balloon.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A catheter assembly, comprising:
   (a) a catheter shaft having a distal end portion and a proximal end portion;
   (b) a main balloon positioned at the distal end portion of the catheter shaft, the main balloon operable between an unexpanded configuration and an expanded configuration;
   (c) a secondary balloon positioned at the distal end portion of the catheter shaft and mounted directly to an outer surface of an expandable portion of the main balloon, the secondary balloon operable between an unexpanded configuration in which the secondary balloon is positioned on the main balloon and an expanded configuration in which the secondary balloon extends radially outward from the outer surface of the main balloon;
   (d) a first structure defining a first inflation lumen, the first inflation lumen extending between the distal end portion and proximal end portion of the catheter shaft and configured to provide inflation fluid to the main balloon;
   (e) a second structure defining a second inflation lumen, the second inflation lumen extending between the distal end portion and proximal end portion of the catheter shaft and configured to provide inflation fluid to the secondary balloon, wherein the second structure extends through a portion of the main balloon; and
   (f) a valve member in fluid communication with the first inflation lumen and the second inflation lumen, the valve member configured to operate the secondary balloon between the unexpanded configuration to the expanded configuration independently of operation of the main balloon between the unexpanded and expanded configurations.

2. The catheter assembly of claim 1, further comprising a stent operably mounted on the main balloon.

3. The catheter assembly of claim 2, wherein the stent includes a proximal open end, a distal open end, and a lateral branch opening, the lateral branch opening positioned at a location between the proximal and distal open ends, and at least a portion of the secondary balloon extends through the lateral branch opening when the secondary balloon is in the expanded configuration.

4. The catheter assembly of claim 1, wherein the secondary balloon is molded integral with the first balloon.

5. The catheter system of claim 1, wherein a distal end of the second structure terminates inside the secondary balloon to provide fluid communication between the second inflation lumen and the secondary balloon.

6. A catheter assembly, comprising:
   (a) a catheter shaft having a proximal end portion and a distal end portion;
   (b) a first balloon member positioned at the distal end portion of the catheter shaft;
   (c) a second balloon member positioned at the distal end portion of the catheter shaft and configured to expand radially outward relative to the first balloon member;
   (d) a first inflation housing defining a first inflation lumen, the first inflation lumen extending from the proximal end portion to the distal end portion of the catheter shaft, the first inflation lumen coupled in fluid communication with the first balloon member;
   (e) a second inflation housing defining a second inflation lumen, the second inflation lumen extending from the proximal end portion to the distal end portion of the catheter shaft, a distal-most end of the second inflation lumen coupled to the second balloon member to provide fluid communication between the second inflation lumen and the second balloon member, wherein a portion of the second inflation lumen extends through the first balloon member; and
   (f) a valve member adjustable between a first position connecting a fluid source in fluid communication with the first inflation lumen while preventing fluid communication between the fluid source and the second inflation lumen, a second position connecting the fluid source in fluid communication with the second inflation lumen while preventing fluid communication between the fluid source and the first inflation lumen, and a third position wherein the fluid source is not in fluid communication with the first and second inflation lumens.

7. The catheter assembly of claim 6, wherein the second balloon member is positioned on the first balloon member.

8. The catheter assembly of claim 6, wherein at least a portion of the first and second inflation lumens are defined within the catheter shaft.

9. The catheter assembly of claim 6, wherein the second balloon member is mounted directly on an outer surface of an expandable portion of the first balloon member, wherein the second balloon member is configured to expand radially from the outer surface of the first balloon member.

* * * * *